United States Patent [19]
Liberti

[11] Patent Number: 5,741,714
[45] Date of Patent: Apr. 21, 1998

[54] DETECTION OF BOUND ANALYTE BY MAGNETIC PARTITIONING AND MASKING

[75] Inventor: Paul A. Liberti, Huntingdon Valley, Pa.

[73] Assignee: Immunivest Corporation, Wilmington, Del.

[21] Appl. No.: 683,812

[22] Filed: Jul. 16, 1996

Related U.S. Application Data

[60] Provisional application No. 60/001,210 Jul. 18, 1995.
[51] Int. Cl.⁶ .................................................. G01N 33/553
[52] U.S. Cl. .................... 436/526; 209/214; 210/695; 210/222; 256/307; 256/317; 422/57; 422/58; 422/68.1; 422/82.08; 435/7.5; 435/7.93; 435/7.94; 435/287.2; 436/526; 436/531; 436/534; 436/805; 436/807
[58] Field of Search ........................ 209/213, 214; 210/695, 222; 356/300, 306, 307; 422/57, 58, 68.1, 82.05, 82.08; 435/7.92, 7.93, 7.94, 287.2, 975, 75; 436/518, 526, 531, 534, 805, 807

[56] References Cited

U.S. PATENT DOCUMENTS

| | | | |
|---|---|---|---|
| 4,446,232 | 5/1984 | Liotta | 436/514 X |
| 4,452,773 | 6/1984 | Molday | 436/526 X |
| 4,517,288 | 5/1985 | Giegel et al. | 43/514 X |
| 4,727,023 | 2/1988 | Wang et al. | 436/519 X |
| 4,752,562 | 6/1988 | Sheiman et al. | 435/5 |
| 4,774,174 | 9/1988 | Giegel et al. | 435/5 |
| 4,786,606 | 11/1988 | Giegel et al. | 436/500 |
| 4,795,698 | 1/1989 | Owen et al. | 435/4 |
| 4,906,439 | 3/1990 | Grenner | 422/56 |
| 4,965,007 | 10/1990 | Yudelson | 252/62.53 |
| 5,108,933 | 4/1992 | Liberti et al. | 436/501 |
| 5,200,084 | 4/1993 | Liberti et al. | 210/695 |
| 5,364,796 | 11/1994 | Blackwood et al. | 436/500 |
| 5,466,574 | 11/1995 | Liberti et al. | 435/5 |

FOREIGN PATENT DOCUMENTS

| | | |
|---|---|---|
| 0173375 | 3/1986 | European Pat. Off. |
| WO9007380 | 7/1990 | WIPO |
| WO9102811 | 3/1991 | WIPO |
| WO 94/11078 | 5/1994 | WIPO |

*Primary Examiner*—Susan Wolski
*Attorney, Agent, or Firm*—Dann, Dorfman, Herrell and Skillman; Henry H. Skillman; Patrick J. Hagan

[57] ABSTRACT

A method and apparatus for determining qualitatively or quantitatively the presence of analyte bound to a separation media without doing a bound/free separation. In the method, the bound fraction is collected in an assay region of a body of liquid which includes the free analyte, and the assay is performed by comparing the radiant-energy response in the assay region to the radiant-energy response in a control region of the body of liquid which is free of bound analyte. The apparatus has a chamber which contains the body of liquid, one or more collection elements and a control element and position in the body of liquid parallel to an opaque wall which has a colliminating slit in registry with each element. Each slit enables sensing of the radiant-energy response from the body of liquid between the slit and its associated elements.

14 Claims, 2 Drawing Sheets

DETECTION OF BOUND ANALYTE BY MAGNETIC PARTITIONING AND MASKING

This application claims priority under 35 U.S.C. §119 (e) to U.S. Provisional Application No. 60/001,210, filed Jul. 18, 1995.

FIELD OF THE INVENTION

This invention is directed to an assay method and apparatus. More specifically, the invention described hereinafter relates to a method and apparatus for determining qualitatively or quantitatively the presence of analyte bound to a separation media employing a principle which permits determination of bound from free analyte without doing a bound/free separation but rather by partitioning the bound such that it can be discriminated from the free. The invention has direct application in competitive and sandwich immunoassay and other assays typically requiring bound/free separation for analysis.

BACKGROUND OF THE INVENTION

The principle of immunoassays is well understood. For low molecular weight analytes such as drugs or metabolites, it is customary to perform competitive immunoassays. Typically, a fixed, limited quantity of specific antibody is allowed to incubate with a known concentration of labeled analyte and patient sample containing some unknown concentration of that analyte. The quantity of label bound to antibody is inversely proportional to the amount of analyte in the test specimen. For quantitation, it is customary to perform a bound/free separation so that labeled analyte associated with the antibody can be detected. There are numerous ways for performing the bound/free separation utilizing a specific binding substance immobilized on a solid phase, e.g., antibody adsorbed or covalently linked to the inside of a tube (coated tube assay), or affixed to a mobile solid phase, e.g., beads, which can either be centrifuged or separated with filters or magnetically. Typically, a separation system should have the characteristics that the separation can easily be performed, excess reagent can be removed easily and non-specifically bound analyte can be washed free of the immobilized antibody with its specifically bound labeled analyte. For analytes which have at least two distinguishable antigenic determinants, a simpler and more precise approach is to perform a sandwich immunoassay, which uses a first antibody directed to one antigenic site as a capture antibody and a second antibody directed at another characteristic determinant as the signal generating antibody. Thus, if the capture antibody is separated from solution, or bound on some solid support, the only way in which signal antibody can be bound to solid support or separated from solution is via analyte. The advantages of sandwich assay are that: (1) signal is directly proportional to analyte concentration on the low end of the analyte curve; (2) extreme sensitivity can be obtained on the low concentration end; (3) sandwich assays are assays of "excesses" since capture antibody and label antibody are typically in excess of analyte and so error is mainly related to accuracy of sample input; and (4) a wide dynamic analyte detection range (as much as 4–5 logs) is possible. Sandwich assay technology, like competitive assay, employ a wide range of systems for performing bound/free separations.

Since bound/free separations require significant manipulation, efforts have been made to avoid bound/free separation altogether or to perform them by as simple a means as possible. Bound/free separations can be avoided entirely if binding of analyte to antibody or inhibition thereof gives rise to a molecular phenomena which can be measured. Such assays are referred to as homogeneous assays, the simplest of which are turbidimetric assays where the turbidity associated with the formation of an immune complex can be enhanced or diminished by analyte either contributing to immune complex formation or inhibiting same. More elegant homogeneous immune assays involve molecular phenomena such as effects relating to rotational diffusion coefficients. As an example, an antibody free in solution will rotate with a rate inversely related to its size and associated hydrodynamic properties, while a low molecular weight analyte will rotate with significantly higher frequency. If the latter bears a fluorescent label, it will have some characteristic fluorescent depolarization, which upon binding will decrease significantly. This principle can be used to determine an unknown quantity of analyte bound to some fixed number of antibodies in the presence of a fixed amount of fluorescently labeled analyte. Fluorescent depolarization assays are employed very effectively for quantitating analytes and particularly those of low molecular weight. Other assays involving quenching of a fluorescent signal upon binding of analyte have been employed. A variety of other homogeneous assays have been devised all of which eliminate the need to perform bound/free separation.

At this point in the evolution of immune assay technology, the most sensitive assays are, indeed, of the heterogeneous kind which require bound/free separation. Hence, some considerable ingenuity has been employed for performing such assays by as simple a means as possible. Several inventions are based on the principle of covalently attaching a fixed quantity of antibody to a well-defined region on a solid support where the latter has reasonable capillary action. See U.S. Pat. Nos. 5,126,242; 4,517,288; 4,786,606; 4,774,174; 4,906,439; 5,364,796; 4,446,232; and 4,752,562. Typically in such assays, specimen and labeled analyte are placed with great precision on such a solid support so as to permit competitive binding to take place on the bound antibodies. Next, solution is added which causes unbound labeled analyte to be carried from the binding region via capillary action. If the analyte is enzyme labeled, and if the liquid employed to "chromatograph" away unbound labeled analyte contains substrate in excess, then a color is developed which will be proportional to the quantity of enzyme specifically bound. Another type of assay operates on a different principle, which effects "bound/free" separation by positioning solid phase antibody in some fraction of the total volume of the system. If that volume fraction where specific binding takes place can be partitioned from the remainder of the system, then it will be possible to quantitate bound signal in the presence of an equilibrium quantity of "free" analyte but the amount of "free" analyte in the detection region will be reduced by the volume element of the immobilized antibody region divided by the total volume of the system. Such assays are referred to as "curtain assays" as this large fraction of unbound analyte and signal is effectively hidden behind a curtain.

Each of the above analytical systems suffers from its own peculiar deficiencies. In the case where capillary action is employed to chromatograph away unbound signal, non-specific binding of signal agent to the matrix can result in substantial background. In the case where signal agent includes labeling antibody or some part thereof as for sandwich assays, non-specific binding becomes a significant concern. Thus, sandwich assays where medium to high sensitivity is required cannot be performed. In the curtain-type assays, there is a finite limit on the smallness of volume fraction where antibody can be bound. Hence, free signal analyte in that region results in low-end sensitivity problems.

Recently, a class of magnetic materials appropriately referred to as ferrofluids have been introduced into immune assay technology. See, for example, U.S. Pat. No. 4,795,698 and International Publication No. WO 91/02811. Ferrofluids are nanosized crystals or crystal clusters which are coated with materials which act as surfactants. Historically, most surfactants were, indeed, detergents; more recently, polymers or proteins have been used in that role. Ferrofluids have a variety of unique properties which include that thermodynamically they act as solutes. Like lyophilic colloids, they interact strongly with solvent and exhibit a variety of most unusual phenomena. With the availability of polymer/protein coated ferrofluids and the use of appropriate coupling chemistries, immune assays in which ferrofluids have been used to perform bound/free separations have been devised. As compared to other capture systems, particularly large magnetic particles (greater than 0.5 microns), ferrofluids provide an advantage with respect to translational and rotational diffusion. Thus, by employing ferrofluids in immune assays, binding reactions proceed at diffusion controlled rates and do not require the constant mixing necessary when larger particles are used.

For polymer/protein coated ferrofluids wherein the crystal core is magnetite, the magnetic gradient to effect separation is inversely related to the numbers of crystals in the clusters. Typically, crystal sizes are 8–15 nm, while after coupling of bioligand, sizes range from about 20 nm to as large as 300–400 nm. Materials synthesized from crystal clusters up to about 120 nm that are well coated with polymer/protein will exhibit colloidal stability for long periods (such materials typically show no signs of settling for as long as six months). As the size decreases within the range for this bioligand-coupled material, which is 20 to 150 nm, such materials become more difficult to separate magnetically. Even high gradient magnetic separation employing very fine stainless steel wires capable of generating gradients of 150–200 kGauss/cm will not effectively separate materials in the 20 nm range. Materials of 40–60 nm, which are probably composed of cores having a cluster of three to six magnetite crystals, can be effectively collected with such gradients.

The above class of materials are beneficially employed in the practice of this invention which takes advantage of two properties of such materials, namely, their ability to diffuse and their ability to be magnetically immobilized. Since diffusion constants are inversely related to colloid size, then smaller bioligand-coupled ferrofluids will have significant advantage over larger materials. Further, smaller diameter materials will, per unit mass, have greater surface areas and the use of such materials in binding reactions will result in additional advantages over larger materials. For example, less material must be inputted into the system; i.e., the binding particles represent a smaller volume fraction. As documented in commonly owned U.S. Pat. No. 5,466,574, due to their surface to mass ratio, the quantities of these ferrofluid particles can be manipulated, such that they will be deposited in a substantially uniform thickness, which may be a substantially single layer of particles, i.e., a monolayer. This property makes possible quantitative signal detection while the particles are immobilized on wires, rods, sheets, or other solid supports.

SUMMARY OF THE INVENTION

The purpose of this invention is to provide a system for performing assays, especially immunoassays, which typically employ receptor binding followed by bound/free separation. The invention provides for the bound fraction to be examined by partitioning it in a region which permits it to be analyzed in the presence of the equilibrium concentration of free analyte. The analysis is performed by sensing the radiant-energy response generated by the bound and free analyte in the partitioned region. The concentration of free analyte, which is quite low by configuration of the system, is measured in another region of the system by sensing its radiant-energy response, and subsequently subtracted from the response of the bound analyte to obtain a more precise measurement. In a preferred embodiment, the invention employs colloidal magnetic materials below 150 nm in size to bind analyte and high gradient magnetic separation to partition the bound analyte. In this preferred embodiment, the ligand-receptor interaction takes place independently of and before the partitioning.

The present invention also provides apparatus which facilitates performing the above-described assays. A suitable apparatus includes a chamber with at least two colliminating apertures and a ferromagnetic collection or a non-ferromagnetic control element in registry with each aperture. The elements may be straight rods having an outside diameter of approximately 0.10 mm, and they are disposed in spaced, parallel relation to their associated aperture which is in the form of a slit having a width less than the diameter of the rod. The ferromagnetic rod may be provided with a barrier coating around the surface area which is not exposed to the aperture, so as to reduce the effective dimensions for collecting the magnetic particles, and increase the sensitivity of the assay. The non-ferromagnetic element may be a non-ferromagnetic component having dimensions identical to the ferromagnetic component, optionally with an identical barrier coating, or it may be a ferromagnetic rod having a barrier coating about its entire periphery.

DETAILED DESCRIPTION OF THE INVENTION

Figure 1:
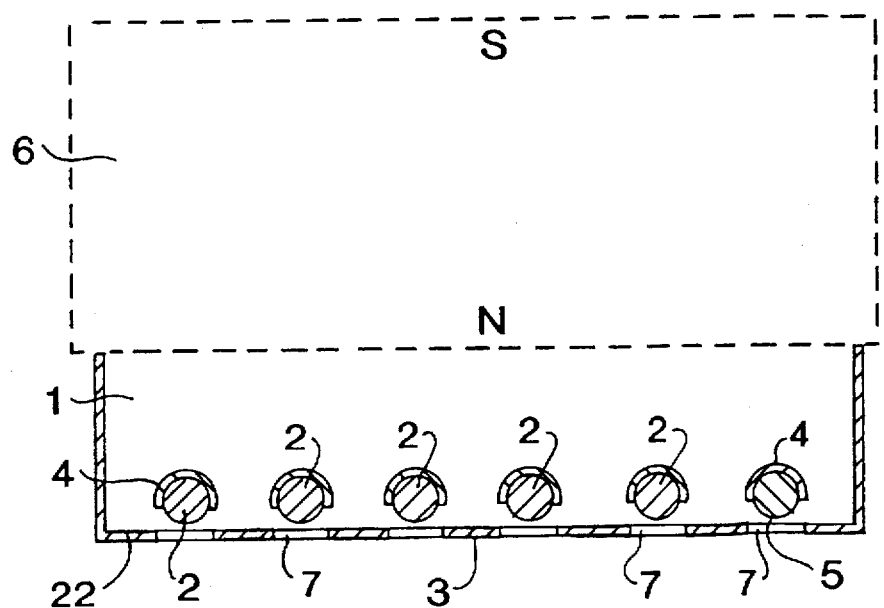
FIG. 1 depicts the cross-sectional view of a device according to the invention, having a plurality of ferromagnetic wires for magnetic collection and one wire for a control.

The purpose of this invention is to provide a system for performing, in a simplified manner, immunoassays or any other assays which typically employ receptor binding followed by a bound/free separation. The invention operates on a principle that allows the bound fraction to be examined by concentrating or partitioning it in a region which permits it to be analyzed in a qualitative or quantitative fashion in the presence of the equilibrium concentration of free analyte. The invention further operates by allowing the ligand-receptor interaction to take place independently and typically before the partitioning. Alternatively ligand-receptor interaction and partitioning can be done simultaneously. The concentration of free analyte, which can be made to be quite low by geometry or configuration of the system, can be measured in another region of the system and subsequently subtracted from the signal of the bound analyte to obtain a more precise measurement. In a preferred embodiment, the invention employs colloidal magnetic materials below 150 nm in size, more properly referred to as bioligand-coupled ferrofluids, to bind analyte and high gradient magnetic separation principles to achieve concentration or partitioning of bound analyte into a region for inspection.

To understand this invention and its goals, it is instructive to examine quantitative ligand receptor binding in view of the commonly used approach which is to perform a bound free separation. The myriad of approaches by which that can be accomplished are well known in the art, and the historical goal has been to perform them in as simple a way as is possible. Key to those approaches is the need to either attach receptor to a support which can be moved or which will keep it from moving, or to transform the receptor into another phase such that it can be separated. In the separation system of this invention the key steps are that receptor ligand binding takes place, ideally in free solution, such that diffusion controlled kinetics of reaction obtain; next, receptor with bound ligand is moved away from the vast majority of the free ligand such that the bound fraction can be determined. Conceptually this task is easily accomplished: receptor is allowed to bind ligand in some appropriately constructed chamber and then, together with its bound ligand, is moved to some part of the chamber where it can be inspected in the absence of the vast majority of free ligand. If the chamber is designed in a manner such that the "inspection" region constitutes some small fraction of the total volume, the remaining task is movement of the receptor with its bound ligand to the inspection region in an efficient and reproducible manner such that quantitative determination can be performed. This can be accomplished by providing a receptor which is selectively movable or attached to some entity which can be selectively moved. In considering all the possible molecular forces which can be exerted on a system from some external source or triggered externally so as to cause receptors to be translated, there is likely none which would not in some instance selectively cause free ligand to be translated as well. By contrast, magnetics in conjunction with magnetic colloids or ferrofluids are not so limited. In particular, high gradient magnetic fields induced upon ferromagnetic elements offers particular advantage to this invention.

To illustrate the principle of the instant invention, a representative configuration of a suitable device for performing a bound/free partitioning assay, is illustrated schematically in FIG. 1. The device 1 is a small chamber, approximately 10 mm×10 mm×3 mm which is sometimes referred to herein as a micro diffusion chamber. The device has side walls and a bottom wall 22 is adapted to contain one or more ferromagnetic element(s) that could include one or more small gauge wires placed near the bottom wall 22 of the chamber in some ordered fashion. FIG. 1 cross-sectionally depicts five such wires 2 arranged generally parallel to one another. These ferromagnetic elements should be disposed far enough above the bottom wall 22 of the chamber that diffusion could proceed unhindered, but close enough that the volume between the elements and chamber bottom wall 22 is negligible when compared to the total volume of the chamber. The wires 2 are furthermore depicted as being partially shielded by a non-magnetic element 4, such as a coating on the region of the wire facing the interior of the micro diffusion chamber. This coating would be thick enough such that when a magnetic gradient is induced on the wire by an external magnetic field, no magnetic material would collect on the portion of the wire which is coated, or on the coating material itself. The coating would be provided along the entire lengths of the wires which are not directly visible to analysis from the bottom wall 22 of the device 1. The bottom of the chamber 1 is fabricated so as not to transmit visible light, except in the area immediately below the ferromagnetic elements. In FIG. 1, the bottom wall 22 of the device has opaque regions 3, and transparent regions 7. The elements could be arranged in rows, such that when viewed from the bottom of the device they would appear as regular stripes being aligned so as to be precisely positioned above the transparent slits. If the masking were done in black and the small gauge ferromagnetic element were magnetic stainless steel, then in viewing the chamber from the bottom, steel stripes would appear against a black background. By choosing the gauge of the wire so that it is as wide or wider than the slit and by precise positioning of the wires over the transparent areas or slits, very little collimated light could be made to pass transversely from the top of the chamber through the floor of such a chamber. Thus, wires serve as a "curtain" for the chamber. Finally, to account for the portion of the labeled material free in solution, i.e., not bound to the magnetic particles or collected onto the ferromagnetic elements, the device includes a control rod 5 made of non-ferromagnetic material, such as aluminum. This control rod is shielded with a non-magnetic element like all of the other wires, and it is of the same overall dimensions as the ferromagnetic wires. The masking of the bottom wall 22 of the chamber adjacent to the control rod is also identical to the other wires. Any signal collected in this region would be background signal, and would be subtracted from signal detected from analyte collected on the other wires.

Figure 2:
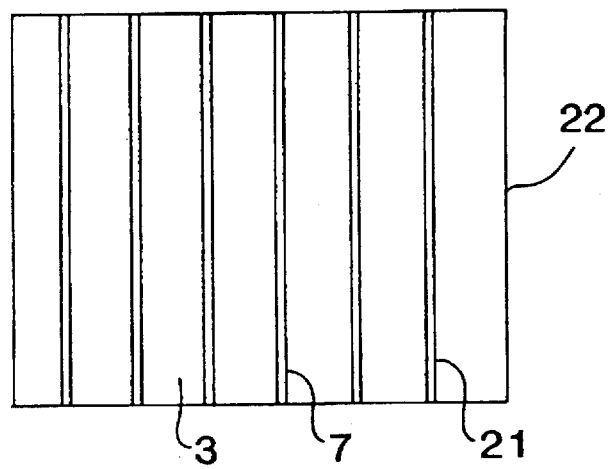
FIG. 2 depicts an inverted plan of the device shown in FIG. 1, with slits for viewing the collected material.

The micro diffusion chamber would contain specific monoclonal antibody (MoAb) coupled to ferrofluid and either detectably labeled analyte (for a competitive assay) or a second MoAb or fragment thereof bearing a detectable label (for a sandwich assay.) In a preferred embodiment, all ferrofluid, antibody, and analyte to be used would be in a dried form that could easily be rehydrated. The micro diffusion chamber could be open at the top for introduction of sample. The sample, which could include patient serum or other bodily fluids would be in a liquid form, which would rehydrate the dried agents in the chamber. Mixing could be accomplished by free diffusion in the liquid form, but appropriate gels or diffusion around or through inert particles could be employed. After mixing, a magnet 6 would be placed on top of the device, thus inducing a magnetic field around the ferromagnetic wires in the chamber. Magnetic material would collect in the region on the wires not covered by the coating 4. For analysis, the chamber would be viewed from the bottom, as shown in FIG. 2. Most of the device would be masked to light passage by regions 3, with the exception of regions 7 through which ferromagnetic element(s) and the material collected upon them could be viewed. Transparent region 21 is provided adjacent to the control, and the signal detected therethrough would be subtracted from the signals detected through transparent regions for the analysis.

High gradient magnetic fields induced on small ferromagnetic wires or small spheres by external magnetic fields have particular advantage in this invention because of the ability to control and manipulate magnetic collection. It is well known that gradient strength produced on such elements are inversely proportional to the radii of such elements and in a practical sense can vary from 200 kGauss/cm down to a few kGauss/cm for large diameter wires or spheres. It should also be noted that the smaller the diameter of the element, the more quickly the field will decay in moving away from the element. Thus smaller elements have a higher "holding" capacity but significantly less "reach" as regards magnetic capture. In the case of small diameter elements, advantage can be taken of the small "reach" as physical barriers can be placed on one side of such an element so as to prevent magnetic collection or alternatively to bias magnetic collection entirely to one side of such an element. The use of ferrofluids in conjunction with the aforementioned high gradient separation principles also has unique advantages. Firstly, ferrofluids by their small size (anywhere from 20 to 180 nm) have large magnetic surface areas per unit mass compared with large magnetic particles. Further, because of their intimate interaction with solvent and their size relative to the change in the magnetic gradient strength induced on small ferromagnetic elements, ferrofluids can easily be made to monolayer on appropriately arranged ferromagnetic collecting elements or, as used in this invention, partitioning elements.

An additional aspect of this invention is the manner in which the ferromagnetic element(s) is (are) utilized. It is well known in the art that a ferromagnetic element placed in a uniform magnetic field will have induced on it high magnetic gradients. Viewed crossectionally, a sphere or round wire will have on it four approximately equal quadrants where surface gradients will alternately serve to attract or repel magnetic materials. By appropriate shielding of a wire, leaving one side bare, or similarly of a sphere where one hemisphere is shielded, such an element will collect magnetic material only on one side when placed in an external magnetic field in the proper orientation. In a preferred embodiment of this invention, the surface on which magnetic collection will be focused is that surface facing toward the bottom or floor of the micro diffusion chamber, i.e. facing the detector. Thus, one could easily envision such a chamber containing an appropriately sized bioligand-coupled ferrofluid which, when the chamber is placed in an external magnetic field transverse to its floor, would result in ferrofluid collection on the bottom-facing surfaces of the wires.

Just as magnetic gradients can be constructed on elements and gradient strength and reach can be adjusted by size and susceptibility of the ferromagnetic element, magnetic colloids can be varied in their ability to be collected versus their ability to diffuse. Large magnetic colloids of the same composition as small ones are significantly more easy to collect in a magnetic gradient. Conversely, smaller colloids diffuse significantly faster than larger ones. Thus, one can envision an induced gradient with little reach which would require a colloid to diffuse quite close to it before capture occurs. If the ferrofluid could be made to give off light or color, then when viewing a chamber fabricated with wires, the bottom of which is masked as described above, strips of light or color on a black background would be seen from below. If that light is a result of bound ligand, then it can be used to quantitate a particular analyte.

One skilled in the art will realize that there is an alternative approach to partition magnetic colloids or for that matter any colloid or macromolecules. For example, in an immunoassay of the sandwich type, sandwiches could be collected or partitioned by having the capture agent (the monoclonal antibody itself or the colloid, ferrofluid or other mobile solid phase to which the MoAb is coupled) biotinylated, such that the capture agent would bind to avidin or streptavidin. If instead of partitioning magnetically on the kinds of ferromagnetic elements described, the collection surfaces of such elements alternatively had bound to them avidin or streptavidin, the same end can be achieved, i.e. the formed sandwiches would in time diffuse to such elements and bind via binding interaction with avidin or steptavidin and partitioning will occur. In such an arrangement the only concern is for the element to be constructed so as to avoid binding of the capture agent (e.g. biotinylated ferrofluid, biotinylated colloid or biotinylated MoAb) before use. It will also be appreciated, however, that such a system suffers from another significant disadvantage which is that formation of sandwiches, i.e. the immune reaction, and capture thereof takes place simultaneously even though one reaction, preferably the binding reaction, can be favored by the geometry of the chamber. Clearly, there is a significant advantage for the binding reaction to be separate and controllable from the capture reaction. For example, some binding reactions require more or less time for completion, depending on various factors such as the concentration of the analyte, and can be aided by different conditions such as temperature. Thus, if binding is separable from capture, as is the case in this invention, then the capture reaction can be done under a set of appropriately favorable conditions different from those used to effect binding. An example of such a situation involves nucleic acid hybridization where that reaction requires heating and can be optimized and controlled by temperature. Hence, the binding reaction could be manipulated accordingly and the subsequent partitioning could be done under optimal reaction conditions, whatever they may be.

The bound fraction to be examined can be concentrated in a region by a variety of means, but when magnetic labeling and partitioning is used, a wire or other ferromagnetic element located in the analysis chamber can have a high gradient magnetic field induced upon it with an external magnet. If a wire were used, a preferred embodiment would be to have an extremely thin wire in the range of 0.01–0.5 mm, which would result in a gradient strong enough to pull magnetic material that is even weakly magnetic. Such a thin wire would have the additional benefit that the high gradient would exist only in a zone narrowly defined around the wire; the magnetic gradient would drop off rapidly. For example, a wire with a diameter of 0.1 mm would have a gradient of 170 kGauss/cm at the surface, but only 6.3 kGauss/cm just 0.1 mm above the surface. This high, but narrow, gradient would result in the ability to coat the wire on one side, preferably the side opposite the analytical detector. This coating would have to be of a non-magnetic material, and it would have to be thick enough that an appreciable magnetic gradient would not exist on it. Therefore, all magnetic material collected would be concentrated on the side of the wire accessible to the analytical detector. Alternatively, such a coating may not be necessary if there is enough signal that approximately one half of the signal could be lost by being inaccessible to the detector.

The wire or ferromagnetic element should be positioned in the micro diffusion chamber in a very precise manner. Since the instant invention involves detection of a bound signal, in the potential presence of some small quantity of free signal, all of which is in the presence of a substrate, the instant invention provides for the "hiding" of most of the unbound or free signal. In a preferred embodiment, the bottom of the reaction chamber is masked from the analytic detector by a an opaque material on the side of the chamber adjacent to the detector. Slits that reveal only the wires are the only breaks in the masking. The wires themselves are placed carefully over the slits so that the wires themselves block any remaining view of the unbound material. One of the wires, or some portion of the wires is made of non magnetic material to act as a control to analyze how much of the unbound signal exists in view of the detector between the wire and the bottom of the chamber. It is very important to place the wires such that the volume of the sample which fall in this portion of the chamber between the wire and the bottom of the chamber is only a small fraction of the total volume of sample.

For a magnetic partitioning of the bound analyte, there is a class of preferred magnetic material which has been applied to bioseparations which have characteristics that place them in a special category. These are nanosized colloids (see U.S. Pat. Nos. 4,452,773 to Molday; 4,795,698 to Owen et al; 4,965,007 to Yudelson; WO 91/02811 by Liberti et al; and WO 90/07380 by Miltenyi.) Such colloids are typically composed of single to multi crystal agglomerates of magnetite coated with polymeric material which make them aqueous compatible. Individual crystals range in size from 8 to 15 nm. The coatings of these materials have sufficient interaction with solvent water to keep them permanently in the colloidal state. Typically, well coated materials below 150 nm will show no evidence of settling for as long as 6 months and even longer. These materials have substantially all the properties of ferrofluids which might be referred to as their non-aqueous compatible counterparts. The important feature of these ferrofluids to the instant invention include their high surface area to mass ratio, and their diffusion kinetics. Because ferrofluids are so small, their surface area to mass ratio is significantly higher than that of larger magnetic particles, such as those sold by Dynal, Rhone-Polenc, or Advanced Magnetics, Inc. Therefore, a significantly reduced mass of magnetic particles, by comparison to such larger particles, is needed to deliver the same amount of specific receptor bound to the magnetic particle. The other key feature of the above-described ferrofluids is their diffusion kinetics. Since they exist in the colloidal state, mixing ferrofluids with other components in solution and their subsequent reaction is determined solely by diffusion kinetics. Simple heating of the mixture as well as gradients that would be induced would be sufficient to mix or cause dissolution. Finally, if the ferrofluid is to be stored in the powdered, or freeze dried form, the "dissolution" or "reconstitution" of the dried powder is expected to be more efficient for a smaller particle.

As referred to above, the magnetic particles which are preferred for the instant invention are directly labeled magnetic particles. Ferrofluids can be easily coated with various antibodies (natural or engineered), avidin, streptavidin, biotin, protein A, haptens, anti-haptens, or other compounds needed for the specific recognition of pre-determined analytes in immunoassays, as well as nucleic acids and derivatives thereof Detection of signal or radiant-energy response may be accomplished through a variety of techniques. One example would be fluorescent detection of a fluorescently labeled antibody, analyte or other small molecule which could be associated with the analyte. Radioactive detection is also a possibility, assuming that the wires and the masking of the bottom of the chamber were of a material impervious to the type of radioactive emission detected. Colormetric detection of a dye attached to the antibody or analyte, possibly enclosed in a liposome, is also envisioned. Chemiluminescent, bioluminescent, electrochemiluminescent, or enzymatic detection is also possible, provided the substrate for the detection reaction become available after the bound/free separation. In the case of base catalyzed reactions or low molecular weight substrates, simple additions could be made as these agents would mix rapidly and would diffuse through the system to the partitioned agent. It would also be possible to trigger substrate release by other means including gel release of substrate, release of substrate from a liposome or other slow release mechanism, release of substrate after a burst of light, electronic, microwave, heat or other radiant energy. Substrate immobilized either on the wire or on the bottom of the micro diffusion chamber is also encompassed within the scope of the instant invention. It is also possible that relatively slow reacting substrate for detection could be lyophilized along with the ferrofluid and other substances used in performing the assay. Conversely, an excess of faster reacting substrate might also provide the desired result. The possibility of using ferromagnetic elements to impart voltage or current for triggering detection reactions also exists. Thus, a variety of methods exist to obtain a readable signal or other radiant-energy response.

There are alternative designs for ferromagnetic elements capable of having generated thereon an appropriate magnetic gradient for this invention. Some considerations for such elements are geometry, ease of manufacture, generation of the appropriate gradient and the need for them to serve as a curtain for the chamber such that any light emanating from the chamber originates from the underside of the ferromagnetic element. Small ferromagnetic spheres positioned in some regular array over an appropriately masked bottom of a diffusion chamber would suffice, providing there is some simple way in which to keep them in position. For one skilled in the art, there would be many ways in which that can be accomplished.

Figure 3:
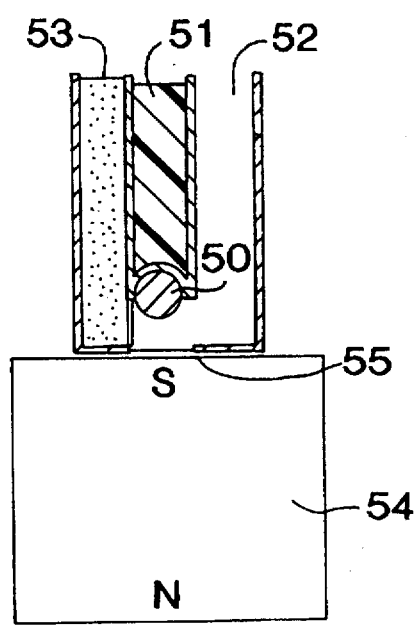
FIG. 3 depicts the cross-sectional view of an alternative embodiment of the invention, with an absorptive pad drawing liquid past a ferromagnetic wire.

An alternative embodiment of this invention is illustrated in FIG. 3. In this device, an absorbent pad or gel 53 draws sample liquid in chamber 52 past a ferromagnetic rod 50, on which a magnetic gradient is induced by the external magnet 54. A portion of rod 50 is shielded by non-magnetic material 51. Labeled material is collected on the ferromagnetic element. The sample chamber can then be removed from the magnet 54 to a sample analysis chamber, in which the sample collected upon the ferromagnetic element is examined through transparent opening or window 55.

Other embodiments of the invention which provide for the use of differently sized wires to discriminate differently sized magnetic particles would also be useful in some cases.

As will be apparent to one skilled in the art, the instant invention is not limited to immunoassay of the traditional type. A further embodiment of the invention provides for use of an assay of this form for molecular diagnostics. Deoxyribonucleic acid (DNA) or ribonucleic acid (RNA) could also be detected by the annealing of magnetically labeled probe. Staining with ethidium bromide or other detection schemes would be used to detect the bound fraction, and thus, the presence of a particular sequence of DNA or RNA could easily be quantified.

The following examples will serve to illustrate the principles of this invention; however, these examples should not be construed as limiting the scope of this invention.

EXAMPLE 1

A Human Chorionic Gonadatropin Assay

To perform an assay requiring bound/free separation, as in a sandwich immunoassay for human chorionic gonadatropin [hCG], a microdiffusion chamber, as described above, might contain, in some dried form, $MoAb_1$ directed to the α subunit of hCG coupled onto ferrofluid and fluoresceinated $MoAb_2$ directed to the β subunit of hCG. Serum sample would be added to the chamber and incubated to allow formation of sandwiches, $MoAb_1$—hCG—Fl—$MoAb_2$, the rate of which will depend on many well known factors, including the size of the ferrofluid and the density of MoAb to which it is coupled. Next, the chamber would be subjected to an external field which will cause the ferrofluid to collect on the undersides of the ferromagnetic elements. Depending on the size and magnetic properties of the ferrofluid, it may be attracted to such surfaces from all points in the chamber or require diffusion to bring it near the collection surface where gradients will attract and hold it. Should the "reach" of the magnetic gradient not be sufficient to attract the ferrofluid from distant parts of the chamber, simple means for inducing fluid motion in such chambers could be employed, as are well known in the art. Once the ferrofluid bearing formed sandwiches are collected or partitioned from the chamber, fluorescence of the labeling antibody can be measured from the bottom of the chamber, emanating from the partitioned ferrofluid which bears labeling fluorescent MoAb. As the concentration of free Fl—MoAb$_2$ will remain the same everywhere in the chamber, the contribution it will make to fluorescence, when observed from the bottom of the chamber, will be related to the volume fraction of the regions under the ferromagnetic partitioning elements. If this fraction is small, signal from free reagent can be negligible. In analysis where very high sensitivity is required, such as in TSH assays, and where high signal-to-noise ratios are required, particularly at the low end of analyte concentration, it will be possible to perform a background control. This can be easily accomplished by substituting one or more of the ferromagnetic elements with an identical structure that employs a non-magnetic metal such as non-magnetic stainless steel, aluminum or copper. With appropriate electronic devices, which are capable of reading signal from closely spaced intervals such as in the chamber described, it would be a relatively easy task to read the "blank" elements and subtract the background.

EXAMPLE 2

Calculation of Ferrofluid and Wire Surface Areas in Magnetic Collection

It is instructive to determine the practicality of design with a high gradient magnetic collector which can monolayer an appropriate amount of ferrofluid for the instant invention. In using ferrofluids for TSH assays, it has been found that 0.5 µg of iron in a ferrofluid with a diameter of 130 nm can effectively capture 70 ng of capture monoclonal antibody. However, to enhance the advantage afforded by the diffusion capability of the agents used in the instant invention, the preferred ferrofluid has a 50 nm diameter, but with the same total surface areas the 130 nm particle described above. It can be calculated that this amount of ferrofluid contains $1.41 \times 10^9$ particles and that, therefore, the surface area of wire necessary to monolayer this amount of ferrofluid is $2.77 \times 10^{-2}$ cm$^2$. For collecting rods of diameters 0.25, 0.12, 0.05, and 0.02 mm, using only 20% of the circumference for collection, rods of 1.7, 3.5, 8.7, 17 cm length, respectively, are required. Chambers as described could easily be constructed to accomodate these lengths. It is obvious that multiple rods of shorter length having the same total length can also be used.

Assumptions:
1. The particles are spherical.
2. All of the iron is in the form of magnetite (Fe$_3$O$_4$) ; for every mg of iron, there is 0.3 mg protein, therefore, there is about 1.4 mg magnetite per mg of iron.
3. The specific volume of magnetite is taken as 0.192 cc/g. The specific volume of protein is 0.714 cc/g.
4. 20% of the wire is available for collection of magnetic material and signal detection.

Abbreviations:

ρ=density of material
υ=partial specific volume
N=number of particles
D=Diameter of particles
S.A.=surface area
M=mass of iron in the particles Formulas:

$$\rho = \frac{g \text{ magnetite} + g \text{ protein}}{v \text{ magnetite} + v \text{ protein}} =$$

$$\frac{g \text{ magnetite} + g \text{ protein}}{(v \text{ magnetite})(g \text{ magnetite}) + (v \text{ protein})(g \text{ protein})}$$

$$N = \frac{M}{\rho \frac{\pi}{6} D^3}$$

Surface area of $N$ spheres = $N\pi D^2$

Area needed for collection of particles $= \frac{N\pi D^2}{4}$

Surface area of a cylinder = (length)$\pi$(diameter)

1. Density of ferrofluid.

$$\begin{aligned} \rho &= \frac{g \text{ magnetite} + g \text{ protein}}{(v \text{ magnetite})(g \text{ magnetite}) + (v \text{ protein})(g \text{ protein})} \\ &= \frac{(1.4 \times 10^{-3} \text{ g}) + (0.3 \times 10^{-3} \text{ g})}{(0.192 \text{ cc/g})(1.4 \times 10^{-3} \text{ g}) + (0.714 \text{ cc/g})(0.3 \times 10^{-3} \text{ g})} \\ &= 3.52 \text{ g/cc} = 3.52 \times 10^{-18} \text{ mg/nm}^3 \end{aligned}$$

2. Ferrofluid mass if 0.5 µg of iron is measured mass=g magnetite+g protein

=(0.5 µg)(1.4 µg magnetite/µg Fe)+(0.5 µg)(0.3 µg protein/ µg Fe)

=0.85 µg ferrofluid

3. Surface area of 0.85 µg of a 130 nm ferrofluid
Surface area of N spheres=$N\pi D^2$ but: $N = \frac{M}{\rho \frac{\pi}{6} D^3}$ Thus:

$$\begin{aligned} \text{Surface area of a sphere} &= \frac{M \pi D^2}{\rho \frac{\pi}{6} D^3} \\ &= \frac{6M}{\rho D} \\ &= \frac{(6)(8.5 \times 10^{-4} \text{ mg})}{(3.52 \times 10^{-18} \text{ mg/nm}^3)(130 \text{ nm})} \\ &= 1.11 \times 10^{-13} \text{ nm}^2 \end{aligned}$$

4. The number of 50 nm particles with this same surface area is

Surface area of a sphere = $N\pi D^2$

-continued $$N = \frac{(S.A.)}{\pi D^2}$$

$$= \frac{(1.11 \times 10^{13} \text{ nm}^2)}{\pi (50 \text{ nm})^2}$$

$$= 1.41 \times 10^9 \text{ particles}$$

5. The surface of wire needed to collect this amount of particles is $$\text{Area for collection} = \frac{N\pi D^2}{4}$$

$$= \frac{(1.41 \times 10^9)\pi (50 \text{ nm})^2}{4}$$

$$= 2.77 \times 10^{12} \text{ nm}^2$$

$$= 2.77 \times 10^{-2} \text{ cm}^2$$

6. If the wire has a 0.1 mm diameter and particles are collected over 20% of the surface of the wire, the length needed to obtain this surface area is Surface area of a cylinder=(20%)(length)π (diameter)

$$\text{length} = \frac{\text{Surface area}}{(20\%)\pi(\text{diameter})}$$

$$= \frac{2.77 \times 10^{-2} \text{ cm}^2}{(20\%)\pi(0.01 \text{ cm})}$$

$$= 4.41 \text{ cm}$$

It will be appreciated from the foregoing description that, according to the embodiment of this invention, an assay is performed by providing a micro diffusion chamber having at least two colliminating apertures. The chamber received a test medium including an immobile solid phase, preferably a ferrofluid, associated with an antibody, a label analyte and a test specimen. Within the chamber and in registry with a first of the apertures, a ferromagnetic element having precisely selected dimensions is immersed in the test medium. One or more of the materials received in the chamber may be freeze-dried. Also within the chamber and immersed in the test medium, a non-ferromagnetic element having dimensions equal to the precisely selected dimensions is positioned in registry with a second of the apertures. A magnetic field is applied to the chamber to cause the magnetic particles of the ferrofluid to collect on the ferromagnetic element. While still immersed in the test medium, the concentration of label from the analyte is detected through each aperture, and the detected concentrations are compared in the presence of an equilibrium concentration of free label.

What is claimed is:

1. An assay apparatus comprising:
   a chamber having a plurality of walls opaque to radiant energy, except for at least one assay aperture and a control aperture which are transparent to radiant energy, said plurality of walls defining a container for a body of fluid having a mobile solid phase component;
   at least one collection element within said chamber, said collection element having a collection area of predetermined dimensions exposed to said body of fluid, said at least one collection area disposed immediately adjacent to a wall of the chamber having said at least one assay aperture to define therebetween a limited assay region; and
   at least one control element within said chamber, said control element having the same overall dimensions as said at least one collection element and having a control area exposed to said body of fluid and disposed immediately adjacent to said control aperture on a wall of the chamber to define therebetween a limited control region for comparison with said assay region,
   said collection area being capable of capturing said mobile solid phase component, and said control area being incapable of capturing said mobile phase component, and
   said limited assay region and said control region constituting a small fraction of said body of fluid.

2. The assay apparatus according to claim 1 wherein said mobile solid phase component is a ferrofluid,
   said collection element comprises a ferromagnetic element having a collection area comprising a limited exposed ferromagnetic surface, said ferromagnetic element having dimensions such that a magnetic gradient sufficient to attract said ferrofluid is induced on said ferromagnetic element in the presence of an external magnetic field, and
   said control element comprises either a non-ferromagnetic element or a ferromagnetic element having a shielding coating covering the entire element.

3. The assay apparatus according to claim 2 wherein said at least one assay aperture and said control aperture are mutually coextensive in length and width with said collection area and said control area, respectively.

4. The assay apparatus according to claim 2 wherein said ferromagnetic element consists of a ferromagnetic wire having a shielding coating covering the element except for the collection area, and the control element consists of a ferromagnetic element having a shielding coating covering the entire element.

5. The assay apparatus according to claim 2 wherein said ferromagnetic element consists of a ferromagnetic wire having a shielding coating covering the element except for the collection area, and the control element consists of a non-ferromagnetic element having a control area.

6. The assay apparatus according to claim 1 including an absorbent material in said chamber adjacent said collection element and said control element to cause said body of fluid to migrate past said collection area and said control area.

7. The assay apparatus according to claim 1 wherein
   said mobile solid phase component is a colloid coupled to biotin,
   said collection area comprises avidin bound to a limited area of said collection element, and
   said movement of said mobile solid phase is achieved by diffusion.

8. An assay method for determining the presence of an analyte in a sample comprising the steps of:
   combining the sample with a first and second specific binding substance in a chamber of an assay apparatus to form a body of fluid to be assayed,
   wherein said first specific binding substance is coupled to a mobile solid phase component and binds to said analyte, and said second specific binding substance is labeled with a detectable label and binds either to said analyte or to said first specific binding substance, and
   wherein said assay apparatus comprises
      a chamber having a plurality of walls opaque to radiant energy, except for at least one assay aperture and a control aperture which are transparent to radiant energy, at least one collection element within said chamber, said collection element having a collection area of predetermined dimensions exposed to said body of fluid, said at least one collection area disposed immediately adjacent to wall of the chamber having said at least one assay aperture to define therebetween a limited assay region, and at least one control element within said chamber, said control element having the same overall dimensions as said at least one collection element and having a control area exposed to said body of fluid and disposed immediately adjacent to said control aperture on a wall of the chamber to define therebetween a limited control region for comparison with said assay region, said collection area being capable of capturing said mobile solid phase component, and said control area being incapable of capturing said mobile phase component, and said limited assay region and said control region constituting a small fraction of said body of fluid;

incubating said body of fluid to produce free label and label bound to said mobile solid phase component in proportion to the amount of analyte in said sample;

producing movement of said mobile solid phase component through said assay region and said control region to provide for capture of said mobile solid phase component onto said collection area, but not onto said control area; and determining the presence of said analyte by detecting, through said assay aperture, a first signal generated by free label in said assay region and said label bound to mobile solid phase component captured onto said collection area, and comparing said first signal with a second signal generated by free label in said control region and detected through said control aperture.

9. The assay method according to claim 8 wherein said mobile solid phase component is a ferrofluid, said collection element comprises a ferromagnetic element having a collection area comprising a limited exposed ferromagnetic surface, said ferromagnetic element having dimensions such that a magnetic gradient sufficient to attract said ferrofluid is induced on said ferromagnetic element in the presence of an external magnetic field, said control element comprises either a non-ferromagnetic element or a ferromagnetic element having a shielding coating covering the entire element, and said movement of said mobile solid phase component is produced by application of an external magnetic field.

10. The assay method according to claim 9 wherein said at least one assay aperture and said control aperture are mutually coextensive in length and width with said collection area and said control area, respectively.

11. The assay method according to claim 9 wherein said ferromagnetic element consists of a ferromagnetic wire having a shielding coating covering the element except for the collection area, and the control element consists of a ferromagnetic element having a shielding coating covering the entire element.

12. The assay method according to claim 9 wherein said ferromagnetic element consists of a ferromagnetic wire having a shielding coating covering the element except for the collection area, and the control element consists of a non-ferromagnetic element having a shielding coating covering the element except for the control area.

13. The assay method according to claim 8 including an absorbent material in said chamber adjacent said collection element and said control element to cause said body of fluid to migrate past said collection area and said control area.

14. The assay method according to claim 8 wherein said mobile solid phase component is a colloid coupled to biotin, said collection area comprises avidin bound to a limited area of said collection element, and said movement of said mobile solid phase is achieved by diffusion.

* * * * *